(12) United States Patent
Wang et al.

(10) Patent No.: US 11,618,857 B1
(45) Date of Patent: Apr. 4, 2023

(54) ELECTRIC FURNACE FOR CRACKING HYDROCARBON FEEDSTOCK WITH HEAT RECOVERY

(71) Applicant: T.EN Process Technology Inc., Houston, TX (US)

(72) Inventors: Qingqi Wang, Rancho Santa Margarita, CA (US); Eric Stanley Wagner, La Canada, CA (US)

(73) Assignee: T.EN Process Technology Inc., Houston, TX (US)

( * ) Notice: Subject to any disclaimer, the term of this patent is extended or adjusted under 35 U.S.C. 154(b) by 0 days.

(21) Appl. No.: 17/727,700

(22) Filed: Apr. 22, 2022

(51) Int. Cl.
*C10G 9/24* (2006.01)
*C07C 4/04* (2006.01)
*C10G 9/36* (2006.01)

(52) U.S. Cl.
CPC .............. *C10G 9/24* (2013.01); *C07C 4/04* (2013.01); *C10G 9/36* (2013.01); *C10G 2300/4081* (2013.01); *C10G 2300/807* (2013.01); *C10G 2400/20* (2013.01)

(58) Field of Classification Search
CPC .... C10G 9/24; C10G 9/36; C10G 2300/4081; C10G 2300/807; C10G 2400/20; C07C 4/04
See application file for complete search history.

(56) References Cited

U.S. PATENT DOCUMENTS 3,654,134 A * 4/1972 Wirth et al. ............ C10B 55/10
208/54

* cited by examiner

*Primary Examiner* — Thuan D Dang
(74) *Attorney, Agent, or Firm* — Locke Lord LLP; Alan B. Clement; Alicia J. Carroll

(57) ABSTRACT

An electric cracking furnace system for converting a hydrocarbon feedstock into cracked gas includes a mixing device for mixing hydrocarbon feedstock with slightly superheated and/or saturated steam. The system includes a steam drum, an electric furnace, a primary transfer line exchanger (PTLE), a secondary transfer line exchanger (STLE), and a tertiary transfer line exchanger (TTLE). The electric furnace includes a feed inlet for a hydrocarbon feedstock-saturated steam mixture and an outlet for a cracked gas. The steam drum includes a saturated steam outlet connected to the mixing device, and a water outlet and a steam inlet both connected to the STLE. The PTLE is configured to preheat the hydrocarbon feedstock-saturated steam mixture before entry into the electric furnace and to cool the cracked gas provided by the electric furnace. The STLE is configured to generate steam and to cool the cracked gas provided by the PTLE.

6 Claims, 1 Drawing Sheet

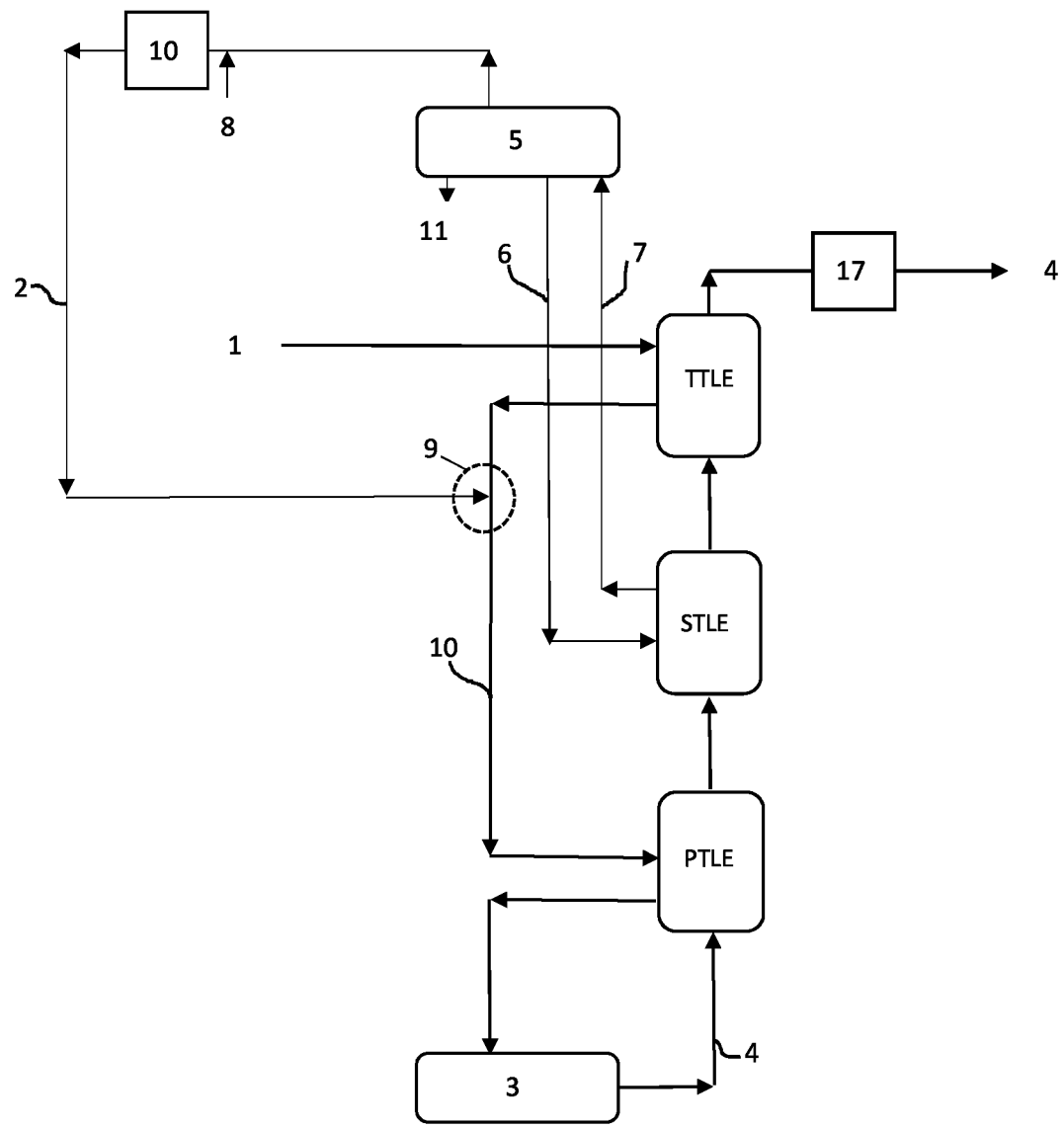

ELECTRIC FURNACE FOR CRACKING HYDROCARBON FEEDSTOCK WITH HEAT RECOVERY

FIELD

The present disclosure relates to an electric cracking furnace system for converting a hydrocarbon feedstock into cracked gas a process for cracking hydrocarbon feedstock using this system. More particularly, the disclosure relates to a process for producing ethylene and propylene from a hydrocarbon feed.

BACKGROUND

In conventional ethylene plants, comprising a fired cracking furnace, enough high pressure (HP) steam is generated to produce power to drive machines and in addition generate dilution steam to suppress the hydrocarbon partial pressure to improve product selectivity and keep coke formation at bay in the cracking reactor.

In the hot section of the plant the dilution steam is traditionally produced from medium pressure (MP) steam that is generated from the HP steam after generating power via one or more steam turbines. In addition, if a primary fractionator is available, which is known for cracking liquid feedstock, the heat recovery of furnace effluent (cracking product) in the quench oil circuit of the primary fractionator, which is a pump-around circuit of said primary fractionator, aids in the generation of dilution steam, allowing more MP steam to be let down to lower pressure levels for maximum power production. At the same time excess heat from the effluent can be recovered in a quench water tower and transferred to low-temperature users via a pump-around loop. This low-level heat is for instance used to preheat furnace feedstock. Further feedstock evaporation is usually done by means of flue gas in the convection section of said conventional cracking furnaces.

In more detail, a conventional gas cracking furnace includes the following features:

Radiant section where the radiant coils are in the firebox (at least one radiant coil) and chemical reactions take place in the radiant coils. Combustion takes place in the firebox via fuel to the burners to provide the heat required for the pyrolysis reactions.

Convection section is used to preheat feed, dilution steam and mixture of feed and dilution steam, generate high pressure steam, preheat boiler feed water. Sometimes, it can also be used to preheat combustion air as air preheater (also called "APH") for fossil fuel combustion at the burners. The purpose of convection section is to recover the available hot flue gas heat from the combustion of fuel and air inside the firebox.

Flue gas mainly contains N2, O2, H2O, CO2, Argon, trace amount of NOx/CO and particular matters (PM2.5, PM5 and PM10). Several ethylene producers have announced the target to reduce CO2 emission by 25% in 2030 and net zero CO2 emission by 2050. Sometimes, DeNOx unit (or called SCR) is installed in the convection section to further reduce NOx generated from the combustion to meet site emission requirements.

Transfer line exchangers (TLEs) are located at the outlet of radiant coils via transfer line to cool down the cracked gas from the outlet of the radiant coils to the desired temperature before leaving the cracking furnace. Transfer line exchangers can be one or multiple exchangers.

Saturated high-pressure steam is generated in the TLEs by quenching the cracked gas via risers and downcomers between TLEs and steam drum.

Saturated high-pressure steam is further heated in the high-pressure steam superheater coils (HPSSH-1 and HPSSH-2) in the convection section to generate superheated high-pressure steam before leaving the cracking furnace.

Dilution steam to the furnaces is supplied from the rest of the plant via dilution steam generation drum. Saturated dilution steam is generated via medium pressure steam as vaporizers and separated in the dilution steam generation drum, then slightly superheated with MP steam before going to the furnace or slightly superheated by injecting higher temperature steam before entering the furnace. In addition, the quench water stripper condensate is preheated with MP steam before going to dilution steam generation drum. Dilution steam is to mix with the preheated dry feed from the upper bank(s) of the convection section. The mixed feed is to further preheated in the lower bank(s) of the convection section to the required radiant coil inlet temperature for cracking in order to reduce coking rate and increase olefins yield at the furnace effluent such as ethylene yield and propylene yield.

The conventional techniques have been considered satisfactory for their intended purpose. However, there is an ever present need for improved electric cracking furnace systems and methods. This disclosure provides a solution for this need.

SUMMARY

Embodiments of the present disclosure aim to improve heat recovery and to simplify the cracking of hydrocarbon feedstock. Embodiments of the present disclosure include an electric cracking furnace system for converting a hydrocarbon feedstock into cracked gas comprising at least: a mixing device for mixing hydrocarbon feedstock with slightly superheated or saturated steam, a steam drum, an electric furnace, a primary transfer line exchanger (PTLE), a secondary transfer line exchanger (STLE), a tertiary transfer line exchanger (TTLE). The electric furnace includes a feed inlet for a hydrocarbon feedstock-slightly superheated or saturated steam mixture and an outlet for the cracked gas. The steam drum comprising a saturated steam outlet connected to the mixing device for mixing hydrocarbon feedstock with saturated steam, and a water outlet and a steam inlet both connected to the secondary transfer line exchanger STLE. The primary transfer line exchanger (PTLE) is configured to preheat the hydrocarbon feedstock-saturated steam mixture before entry into the electric furnace and to cool the cracked gas provided by the electric furnace. The secondary transfer line exchanger (STLE) configured to generate steam and to cool the cracked gas provided by the primary transfer line exchanger (PTLE). The tertiary transfer line exchanger (TTLE) configured to preheat the hydrocarbon feedstock before its mixing with saturated steam and to cool the cracked gas provided by the secondary transfer line exchanger (STLE). The electric cracking furnace system can include a compressor of the cracked gas with electric turbine. The secondary transfer line exchanger (STLE) is configured to generate steam at a pressure between 4 and 15 $kg/cm^2g$. The electric cracking furnace system can include a heat exchanger to preheat the saturated steam provided by the steam drum upstream of the mixing device. The electric cracking furnace system can include a second mixing device for mixing the saturated steam provided by the steam drum with preheated steam upstream of the mixing device. The electric cracking furnace system can include N electric furnaces, N to 10N primary transfer line exchangers PTLE, N to 2N secondary transfer line exchangers STLE, N to 2N tertiary transfer line exchangers TILE with N≥2 and N or less than N steam drum with N≥2.

In accordance with another aspect, a process for cracking hydrocarbon feedstock in an electric cracking furnace system can include preheating a hydrocarbon feedstock in a tertiary transfer line exchanger (TTLE). The process includes mixing the preheated hydrocarbon feedstock with at least one of saturated, or slightly superheated steam to generate at least one of a hydrocarbon feedstock-saturated steam mixture or a hydrocarbon feedstock-slightly superheated steam mixture. The process includes preheating at least one of the hydrocarbon feedstock-saturated steam mixture or the hydrocarbon feedstock-slightly superheated steam mixture in a primary transfer line exchanger (PTLE). The process includes cracking the preheated hydrocarbon feedstock-saturated steam mixture or the hydrocarbon feedstock-slightly superheated steam mixture in the electric furnace to produce a cracked gas. The process includes providing a first cooling of the cracked gas in the primary transfer line exchanger (PTLE). The process includes providing a second cooling of the cracked gas exiting the primary transfer line exchanger (PTLE) in a secondary transfer line exchanger (STLE). The process includes producing steam in the secondary transfer line exchanger (STLE). The process includes providing a third cooling of the cracked gas exiting the secondary transfer line exchanger (STLE) in the tertiary transfer line exchanger (TTLE).

The hydrocarbon feedstock can be a dry gas. The process can include producing saturated or slightly superheated steam in a steam drum. The steam produced in the secondary transfer line exchanger (STLE) can be generated from water coming from a steam drum. The steam produced in the secondary transfer line exchanger (STLE) can be sent into the steam drum. Preheating at least one of the hydrocarbon feedstock-saturated steam mixture or the hydrocarbon feedstock-slightly superheated steam mixture can include preheating at a temperature between 180° C. and 300° C. Preheating at least one of the hydrocarbon feedstock-saturated steam mixture or the hydrocarbon feedstock-slightly superheated steam mixture can include preheating at a temperature between 200° C. and 260° C. The steam produced in the secondary transfer line exchanger (STLE) is at a pressure between 4 kg/cm$^2$ and 15 kg/cm$^2$g, or at a pressure between 6 kg/cm$^2$g and 8 kg/cm$^2$g.

Cooling the cracked gas in the primary transfer line exchanger (PTLE) can include cooling the cracked gas at a temperature between 750° C. and 900° C., or at a temperature between 820° C. and 875° C. Cooling the cracked gas in the secondary transfer line exchanger (STLE) includes cooling the cracked gas at a temperature between 375° C. and 600° C., or between 420° C. and 520° C. These and other features of the systems and methods of the subject disclosure will become more readily apparent to those skilled in the art from the following detailed description of the preferred embodiments taken in conjunction with the drawings.

BRIEF DESCRIPTION OF THE DRAWINGS

So that those skilled in the art to which the subject disclosure appertains will readily understand how to make and use the devices and methods of the subject disclosure without undue experimentation, preferred embodiments thereof will be described in detail herein below with reference to certain FIGURES, wherein:

FIG. 1 is a schematic depiction of an embodiment of an electric furnace system constructed in accordance with the disclosure, showing one primary transfer line exchanger, one secondary transfer line exchanger and one tertiary transfer line exchanger.

DETAILED DESCRIPTION

Reference will now be made to the drawings wherein like reference numerals identify similar structural features or aspects of the subject disclosure. For purposes of explanation and illustration, and not limitation, a schematic view of an exemplary embodiment of an electric cracking furnace system in accordance with the disclosure is shown in FIG. 1 and is designated generally by reference character 100. Other embodiments of the electric cracking furnace system in accordance with the disclosure, or aspects thereof, are described below. The systems and methods described herein can be used to improve heat recovery and to simplify the cracking of hydrocarbon feedstock. Embodiments of the present disclosure aim to improve heat recovery and to simplify the cracking of hydrocarbon feedstock.

Embodiments of the present disclosure include an electric cracking furnace system for converting a hydrocarbon feedstock 1 into cracked gas 4 comprising at least:

A mixing device 9 for mixing hydrocarbon feedstock 1 with slightly superheated or saturated steam 2,
A steam drum 5,
An electric furnace 3,
A primary transfer line exchanger (PTLE),
A secondary transfer line exchanger (STLE),
A tertiary transfer exchanger (TTLE)
  With
    The electric furnace 3 comprising a feed inlet for a hydrocarbon feedstock-slightly superheated or saturated steam mixture 10 and an outlet for the cracked gas 4,
    The steam drum 5 comprising a saturated steam outlet connected to the mixing device 9 for mixing hydrocarbon feedstock with saturated steam, and a water 6 outlet and a steam 7 inlet both connected to the secondary transfer line exchanger STLE,
    The primary transfer line exchanger (PTLE) configured to preheat the hydrocarbon feedstock-saturated steam mixture before entry into the electric furnace 3 and to cool the cracked gas 4 provided by the electric furnace 3,
    The secondary transfer line exchanger (STLE) configured to generate steam 7 and to cool the cracked gas 4 provided by the primary transfer line exchanger (PTLE).
    The tertiary transfer line exchanger (TTLE) configured to preheat the hydrocarbon feedstock 1 before its mixing with saturated steam 2 and to cool the cracked gas 4 provided by the secondary transfer line exchanger (STLE).

FIG. 1 depicts an electric furnace system 100 according to an embodiment of the present disclosure. The electric furnace system 100 includes one primary transfer line exchanger, one secondary transfer line exchanger and one tertiary transfer line exchanger.

The steam drum 5 includes a blowdown outlet 11.

According to embodiments of the present disclosure, a superheated steam is a steam having a temperature above the temperature of the saturated steam, preferably the difference between the temperature of saturated steam and the temperature of superheated steam is less than 10° C.

According to embodiments of the present disclosure, an "electric furnace" is an electrically-powered pyrolysis reactor.

A variety of suitable devices can be used as mixing device 9. According to embodiments of the present disclosure, mixing device 9 can be a gas mixer with mechanical mixing valve, a gas mixer with electrical mixing valve, gas mixers with pneumatic flow rate controller, gas mixers with flow rate controllers (e.g., a mass flow controller), or the like.

The transfer line exchanger (TLE) is a heat exchanger arranged to cool down or quench the cracked gas. Heating the feedstock in the transfer line exchangers, according to embodiments of the present disclosure, using waste heat of the cracked gas in the transfer line exchanger, instead of heating the feedstock in the convection section, as is done in prior art systems, can allow a furnace efficiency to be increased significantly. The furnace efficiency is the ratio between the heat absorbed by at least one radiant coil for the conversion of the hydrocarbon feedstock to the cracked gas by means of pyrolysis, which is an endothermic reaction, and the heat released by the combustion process in the combustion zone, based on a lower heating value of 25° C. or 15.6° C.

The optimum inlet temperature of the feedstock into the radiant section is determined by the thermal stability of the feedstock, as is known to the person skilled in the art. Ideally the feedstock enters the radiant section at a temperature just below the point where the pyrolysis reaction starts. If the feedstock inlet temperature is too low, additional heat is required to heat up the feedstock in the radiant section, increasing the heat required to be supplied in the radiant section and the corresponding power consumption. If the feedstock inlet temperature is too high the pyrolysis may already start in the transfer line exchangers or in the pipes which is undesirable, as the reaction is associated with the formation of cokes, which cannot be removed easily.

The secondary transfer line exchanger (STLE) is placed in series after the primary transfer line exchanger (PTLE) to further cool down the cracked gas from the electric furnace. While the primary transfer line exchanger (PTLE) is configured to heat the feedstock before entry into the electric furnace, the secondary transfer line exchanger is configured to partially vaporize the boiler water by quenching the cracked gas. The system can comprise one or more secondary heat exchangers. The system comprises a steam drum which is connected to the secondary transfer line exchanger (STLE). Boiler water flows from the steam drum of the cracking furnace system to the secondary transfer line exchanger. After being partially vaporized inside one of the secondary transfer line exchanger (STLE), the mixture of steam and water can be redirected to the steam drum, where steam can be separated from remaining liquid water.

The electric cracking furnace system can comprise advantageously several primary transfer line exchangers (PTLE).

Depending on the embodiment, the electric cracking furnace system according to the embodiments of the present disclosure can comprise one or more of the following features:
The electric cracking furnace system comprises at least a compressor 17 of the cracked gas 4 with electric turbine. Preferably the compressor comprises multiple stages; advantageously between 1 and 5 stages;

the secondary transfer line exchanger (STLE) is configured to generate steam 7 at a pressure between 4 and 15 $kg/cm^2g$ the electric cracking furnace system comprises a heat exchanger 12 to preheat the saturated steam provided by the steam drum or a second mixing device for mixing the saturated steam provided by the steam drum with preheated steam 8 upstream of mixing device 9 for mixing hydrocarbon feedstock with saturated or slightly superheated steam.

The electric cracking furnace system comprises N electric furnaces 3, N to 10N primary transfer line exchangers PTLE, N to 2N secondary transfer line exchangers STLE, N to 2N tertiary transfer line exchangers TTLE with N≥2 and N or less than N steam drum 5 with N≥2. On the other words, the electric cracking furnace system also comprises just one steam drum with multiple risers (minimum one) and downcomers (minimum one) for one or more than one electric furnaces. Another object of embodiments of the present disclosure is a process for cracking hydrocarbon feedstock in an electric cracking furnace system as defined in the present disclosure, the process comprising:

a) A preheating step of the hydrocarbon feedstock 1 in the tertiary transfer line exchanger (TTLE);
b) A mixing step 9 of the preheated hydrocarbon feedstock 1 with saturated or slightly superheated steam 2;
c) A preheating step of the hydrocarbon feedstock-saturated or slightly superheated steam mixture 10 provided at step a) in the primary transfer line exchanger (PTLE);
d) A cracking step of the mixture preheated at step b) in the electric furnace 3 to produce cracked gas 4;
e) A first cool step of the cracked gas 4 in the primary transfer line exchanger (PTLE);
f) A second cool step of the cracked gas 4 exiting the primary transfer line exchanger (PTLE) in the secondary transfer line exchanger (STLE);
g) A production step of steam 7 in the secondary transfer line exchanger (STLE); and
h) a third cool step of the cracked gas 4 exiting the secondary transfer line exchanger (STLE) in the tertiary transfer line exchanger (TTLE).

Depending on the embodiment, the process for cracking hydrocarbon feedstock according to the present disclosure can comprise one or more of the following features:
the hydrocarbon feedstock 1 is a dry gas. Preferably, the hydrocarbon feedstock 1 comprises between of 50% vol and 100% vol ethane and between of 50% vol and 0% vol propane, more preferably between of 80% vol and 100% vol ethane and between of 20% vol and 0% vol propane;
the process for cracking hydrocarbon feedstock comprises a production step of saturated or slightly superheated steam 2 in the steam drum 5.
the steam 7 produced at step g) is generated from water 6 coming from steam drum 5.
the steam 7 produced at step g) is sent into the steam drum 5.
at step c) the hydrocarbon feedstock-saturated or slightly superheated steam mixture 10 is preheated at a temperature between 180° C. and 300° C., preferably at a temperature between 200° C. and 260° C.
at step g) the steam 7 produced is at a pressure between 4 $kg/cm^2$ and 15 $kg/cm^2g$, preferably at a pressure between 6 $kg/cm^2g$ and 8 $kg/cm^2g$.

at step e) the cracked gas 4 is cooled at a temperature between 750° C. and 900° C., preferably at a temperature between 820° C. and 875° C.

at step f) the cracked gas (4) is cooled at a temperature between 375° C. and 600° C., preferably at a temperature between 420° C. and 520° C.

the steam 7 produced at step g) is generated from water 6 coming from steam drum 5.

the steam 7 produced at step g) is sent into the steam drum 5.

Electric furnace, no convection section, no flue gas generation, and therefore, no emission such as NOx/CO/PM and CO2 as compared with conventional cracking furnaces supplied with fossil fuel/air for combustion via burners. Instead, electric furnace is to supply heat in the cracking radiant section by electrical resistance heating. Heat input can be controlled by the power generation along the radiant coils. Unlike conventional furnace design, transfer line exchangers (TLEs) are used to generate high pressure steam (HP). In embodiments of the present disclosure, none of the transfer line exchangers are used to generate high pressure steam. Instead, one of the transfer line exchangers are used to generate dilution steam by quenching the cracked gas effluent. This is the role of the second transfer line exchanger (STLE). Other two transfer line exchangers are used to: 1. preheat dry feed by quenching the cracked gas effluent. This is the role of the tertiary line exchanger (TTLE) 2. further preheat mixed feed (mixture of dilution steam and dry feed) by quenching cracked gas effluent before going to the radiant coil inlet for cracking. This is the role of the primary transfer line exchanger (PTLE). This process according to embodiments of the present disclosure applies for gas feed cracking —mainly ethane, ethane/propane mix, propane gas cracking furnaces.

It is well known that mixing dilution steam with feed in the convection section in the cracking furnace is required to reduce coking rate in the radiant coil and increase olefins yield as the primary reactions towards olefins are favorable with lower partial pressure of hydrocarbon. The overall TLE duty for gas cracking furnace is higher than the duty required for preheating dry hydrocarbon (HC) feed and mixed feed (HC+DS). In order to achieve efficient TLE heat recovery, it is important to recovery the amount of extra heat from the TLEs for electric furnace design. Using transfer line exchanger (TLE) as a boiler from furnace to generate dilution steam in the dilution steam generation drum by quenching the cracked gas effluent is a new idea.

Furthermore, when the dilution steam generation drum is connected to the TLE to generate dilution steam, such application can be done with one drum by connecting that TLE via a riser and a downcomer from each electric furnace or can be shared with multiple electric furnaces by connecting to various TLEs (Dilution Steam-Effluent Exchangers) via multiple risers and downcomers to be cost effective. The downcomer is the connecting piping from steam drum to TLE, fluid in downcomer is in saturated liquid phase (saturated water) to provide liquid head (driving force for natural circulation). And the riser is the connecting piping from TLE back to steam drum to make a closed loop of steam/TLE system, fluid in the riser is in two phase flow (water/steam) after exchanging heat in the TLE and generate steam. Liquid head in the downcomer needs to overcome the overall system pressure drop (TLE and piping pressure loss) to form natural circulation between steam drum and TLE.

For example, for conventional ethane, ethane/propane mix, propane cracking furnace, two types of TLEs are typically used. Primary and/or secondary TLEs are used to generate saturated high-pressure steam and then superheated steam in the convection section before being exported from the furnace, superheated steam can go to the steam turbine of the cracked gas compressor to generate electricity for compression. Tertiary TLE is used to preheat boiler feed water before going to the convection section for further preheating before going to the high-pressure steam drum to provide heat for steam generation. The traditional concept is to use common dilution steam generation drum from the rest of plant to generate dilution steam via exchanging heat with medium pressure steam (MP) in the multiple exchangers and then slightly superheat with MP steam (e.g. 15° F. (8° C.)) before going to the furnace. In addition, MP steam is often used to preheat quench water stripper condensate before going to the dilution steam generation drum in order to provide the available heat to the dilution steam generation drum.

However, for electric furnace, there is no convection section, saturated high-pressure steam cannot go to the convection section for superheating. Saturated high-pressure steam has no usage. The preheated BFW (BFW=boiler feed water) from Tertiary TLE if applied also cannot go to convection section. Therefore, minimization of HP steam generation or no HP steam generation from the cracking furnace is essential as there is no home for the HP steam. All the three major cracked gas, ethylene and propylene refrigeration compressors can be all made with electric, rather than steam turbine. These are typical 3 main compressors in ethylene plant (namely: cracked gas, ethylene refrigeration and propylene refrigeration compressors). As there could be not much steam or no steam generated from the furnace if heat to the radiant coils is provided with electric rather than fossil fuel. Normally, in conventional furnace, HP steam is generated from the cracking furnace, if the cracking furnace becomes electric furnace, no HP steam is generated from TLE, therefore, the cracked gas compressor normally needs to be electric driven rather than steam turbine driven (unless there is steam from other sources except from ethylene cracking furnaces). Other two compressors (ethylene and/or propylene refrigeration compressors) can also be electric if there are no available or not enough steam generated in the plant. If HP or MP steam generation is used in lieu of DS steam generation for secondary TLE (S-TLE) to achieve the required heat recovery, the saturated steam must be superheated in order to be useful, then additional steam superheater is required. In addition, a new steam turbine may be required if HP steam is used to generate lower steam levels. If zero emission is required, steam superheater must be with electric heater or fired with 100% H2 to minimize CO2 emission in the furnace stack. Besides that, dilution steam generation system from the rest of plant is still required. This makes electric furnace and its steam supply system costly. In any case, dilution steam is still always required for cracking to reduce coking rate and increase olefins yield such as ethylene yield and propylene yield.

Therefore, the solution of the embodiments of the present disclosure enables the optimal heat recovery of TLEs in the electric furnace application to maintain the same overall heat recovery in the TLEs as convectional cracking furnace in order not to overload the downstream quench tower system.

With the application of the S-TLE to generate dilution steam, cracked gas outlet temperature after Tertiary TLE can be the same as the Tertiary TLE outlet temperature from conventional cracking furnace design (e.g. about 149 to 177° C. for ethane cracking). Therefore, the required overall heat recovery is achieved in the TLEs to reduce the load in the downstream quench tower and, therefore, less cooling quench water circulation flow is needed.

For gas cracking electric furnace (ethane, ethane/propane mix, propane), dry feed can be heated in the tertiary TLE, and mixed feed can be further heated in the primary TLE by quenching the hot cracked gas, dilution steam can be generated via secondary TLE, together with dilution steam generation drum, also by quenching the hot cracked gas. The saturated dilution steam from dilution steam generation drum can be slightly superheated (e.g. 15° F. (8.3° C.)) with a small MP steam exchanger or a small electric heater or injecting some available steam for superheating before going to the furnace.

The advantages for this innovation are summarized as below:
i. Fully utilize the available overall heat duty from transfer line exchangers (TLEs) to achieve optimal heat recovery for the electric furnace design, generate dilution steam via one of the TLEs (usually secondary TLE, this TLE is named as "Dilution Steam-Effluent Exchanger") together with dilution steam generation drum to feedback to the furnace directly as a self-contained, closed loop system for the electric furnace design.
ii. This application can be extended for the application of multiple furnaces with one common dilution steam generation drum. Multiple TLEs can be connected to this drum via multiple risers/downcomers to generate dilution steam to feedback to the multiple furnaces in order to further reduce the overall equipment count as required.
iii. By applying this innovation, no high-pressure or medium to high pressure steam generation is required because it is also not useful for electric furnace application. In the electric furnace design, it is essential to minimize or eliminate HP steam production from the TLEs of the furnace.
iv. Traditional dilution steam generation system from the rest of the plant (or called the recovery section of the ethylene plant) is then not required as furnace can effectively generate dilution steam by itself. Since we use the available duty from Dilution Steam-Effluent Exchanger to generate dilution steam, it saves the energy for using MP steam in multiple dilution steam generators to produce dilution steam. These multiple dilution steam generators are then not needed. It also saves MP steam consumption significantly.
v. Since the operating pressure for dilution steam is generally only 85-115 psig (6-8 kg/cm²g), much lower than HP steam pressure (e.g. nominal 1500 psig system (steam pressure can be ranged from 400 psig to 2000 psig)), this creates excellent heat transfer to cool down the cracked gas for this TLE design. In addition, it has a good cost benefit due to much lower design pressure and smaller heat exchanger. Furthermore, the elevation of dilution steam generation drum becomes lower due to lower operating pressure, this saves the piping for the risers and downcomers and also saves the structure steel material as compared with the conventional TLE with high pressure steam system.

The invention claimed is:

1. An electric cracking furnace system for converting a hydrocarbon feedstock into cracked gas comprising at least:
   a mixing device for mixing hydrocarbon feedstock with slightly superheated or saturated steam,
   a steam drum,
   an electric furnace,
   a primary transfer line exchanger (PTLE),
   a secondary transfer line exchanger (STLE),
   a tertiary transfer line exchanger (TTLE),
   the electric furnace comprising a feed inlet for a hydrocarbon feedstock-saturated steam mixture and an outlet for a cracked gas,
   the steam drum comprising a saturated steam outlet connected to the mixing device, and a water outlet and a steam inlet both connected to the secondary transfer line exchanger (STLE),
   the primary transfer line exchanger (PTLE) configured to preheat the hydrocarbon feedstock-saturated steam mixture before entry into the electric furnace and to cool the cracked gas provided by the electric furnace,
   the secondary transfer line exchanger (STLE) configured to generate steam and to cool the cracked gas provided by the primary transfer line (PTLE), and
   the tertiary transfer line exchanger (TTLE) configured to preheat the hydrocarbon feedstock before its mixing with saturated steam and to cool the cracked gas provided by the secondary transfer line exchanger (STLE).

2. The electric cracking furnace system according to claim 1, comprising at least a compressor of the cracked gas with electric turbine.

3. The electric cracking furnace system according to claim 1, wherein the secondary transfer line exchanger (STLE) is configured to generate steam at a pressure between 4 and 15 kg/cm²g.

4. The electric cracking furnace system according to claim 1, comprising a heat exchanger to preheat the saturated steam provided by the steam drum upstream of the mixing device.

5. The electric cracking furnace system according to claim 1, comprising a second mixing device for mixing the saturated steam provided by the steam drum with preheated steam upstream of the mixing device.

6. The electric cracking furnace system according to claim 1, comprising N electric furnaces, N to 10N primary transfer line exchangers PTLE, N to 2N secondary transfer line exchangers STLE, N to 2N tertiary transfer line exchangers TTLE with N≥2 and N or less than N steam drum with N≥2.

* * * * *